United States Patent [19]

Harman, III

[11] 4,379,402

[45] Apr. 12, 1983

[54] GAS ANALYSIS INSTRUMENT HAVING FLOW RATE COMPENSATION

[75] Inventor: John N. Harman, III, Placentia, Calif.

[73] Assignee: Beckman Instruments, Inc., Fullerton, Calif.

[21] Appl. No.: 227,332

[22] Filed: Jan. 22, 1981

[51] Int. Cl.³ .......................................... G01N 31/00
[52] U.S. Cl. ...................................... 73/23; 422/52; 422/54; 422/98
[58] Field of Search ................. 73/23; 422/52, 54, 83, 422/93, 98; 23/230 PC

[56] References Cited

U.S. PATENT DOCUMENTS

| | | | |
|---|---|---|---|
| 3,250,469 | 5/1966 | Colston | 235/200 |
| 3,349,619 | 10/1967 | Millar | 73/205 |
| 3,537,296 | 11/1970 | Gamache | 73/23 |
| 3,760,831 | 9/1973 | Coldin | 422/52 |
| 4,015,473 | 4/1977 | Kleuters et al. | 73/205 L |
| 4,118,973 | 10/1978 | Tucker et al. | 73/55 |
| 4,190,368 | 2/1980 | Etess | 422/52 |
| 4,257,777 | 3/1981 | Dymond | 422/52 |

OTHER PUBLICATIONS

Article entitled "Evaluation of the Measurement of Oxides of Nitrogen in Combustion Products by the Chemiluminescence Method", by J. D. Allen, *Journal of the Institute of Fuel*, vol. 47, p. 275, (1974).

Primary Examiner—Herbert Goldstein
Attorney, Agent, or Firm—R. J. Steinmeyer; P. R. Harder; Edward C. Jason

[57] ABSTRACT

An apparatus for compensating for changes in the mass flow rate of a sample gas stream in gas analysis instruments having outputs that are calibrated in terms of the concentration of a component of the sample stream. In instruments in which a pressure regulated sample gas stream is applied to a detector assembly through a flow restrictor such as a sample capillary, a gas flow sensor is connected in series with the flow restrictor to develop a correction signal that varies in accordance with the mass flow rate of the sample stream. A correcting circuit combines the correction signal from the flow sensor with the output signal from the detector assembly to produce a corrected output signal that correctly indicates the concentration of the component of interest.

16 Claims, 6 Drawing Figures

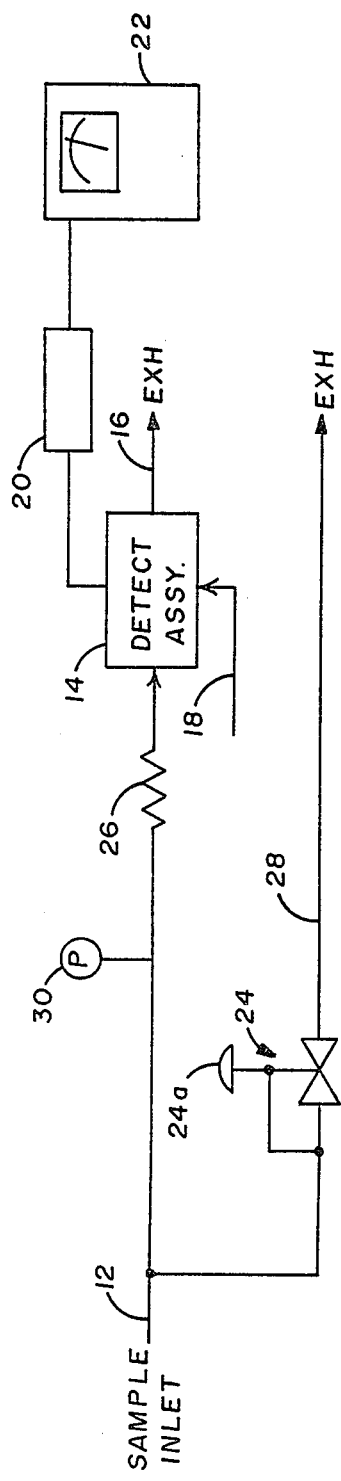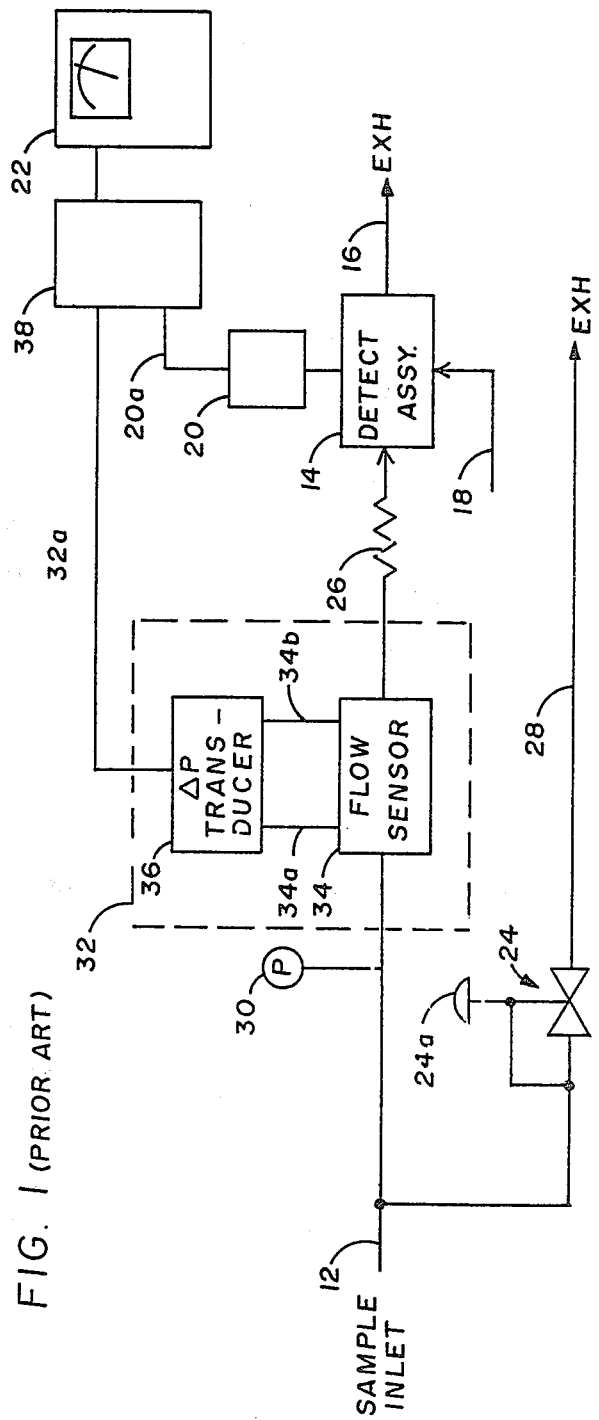
FIG. 1 (PRIOR ART)
FIG. 2

GAS ANALYSIS INSTRUMENT HAVING FLOW RATE COMPENSATION

BACKGROUND OF THE INVENTION

Under circumstances where it is necessary to provide a continuous indication of the concentration of one component of a sample gas stream, it has long been the practice to use detection techniques that are responsive to the mass rate of flow of the component of interest. In analyzers of the chemiluminescent type, for example, the concentration of the component of interest is determined by measuring the intensity of the light emitted by a mixture of the sample gas stream with a substance that is photochemically reactive with the component of interest. In such instruments the intensity of the light emitted at each instant is dependent upon the total number of photochemical events that are occurring within the detection chamber at that instant and, therefore, upon the mass rate of flow of the component of interest. The latter rate is, in turn, dependent upon the overall or bulk mass rate of flow of the sample gas stream.

Similarly, in instruments of the flame-ionization type, a sample gas-fuel mixture is burned in such a way that the component of interest produces ionized particles in the region between a pair of strongly biased electrodes. The concentration of the component of interest at each instant is then inferred from the instantaneous magnitude of the current flow in an external circuit that connects the electrodes. As a result, the measured quantity of the component of interest at each instant is dependent upon the number of charged particles that are present in the detection chamber at each instant and, therefore, upon the mass flow rate of the component of interest. The latter rate is, in turn, dependent upon the bulk mass rate of flow of the sample gas stream.

In spite of the fact that the detected quantity of a component of interest is dependent on the bulk mass rate of flow of the sample stream that includes it, it has long been the practice to display the results of the measurement process in terms of the concentration of the component of interest, commonly expressed in parts per million. This choice of concentration as an output variable creates a potential source of error, however, since concentration is a quantity that is not dependent upon the bulk mass rate of flow of the sample gas stream, concentration being merely a measure of the relative number of molecules of each species in the sample stream.

In order to prevent real changes in the concentration of the component of interest from being confused with the apparent changes in concentration that result from changes in the bulk mass flow rate of the sample stream, it has been the practice to take steps to fix the rate of flow of the sample stream at a suitable constant value. The most commonly used method for accomplishing this involves the use of a pressure regulator for regulating the pressure of the sample gas stream and the connection of a flow restrictor such as a sample capillary between the pressure regulator and the detection chamber. Together these elements operate (in a manner analogous to that in which a regulated voltage source in series with a fixed resistance provides a fixed current in an external circuit of lower resistance) to provide a constant rate of flow of sample gas through the instrument.

The problem with the above described flow regulation scheme is that, strictly speaking, the pressure drop or difference in pressure across the sample capillary is proportional not to the bulk mass rate of flow of the sample stream therethrough, but rather to the product of the bulk mass rate of flow and the bulk kinematic viscosity of the gas in the sample stream. As a result, even with a constant pressure difference across the capillary, any changes in the bulk viscosity of the sample gas from the value existing at the time the instrument is calibrated (e.g. changes in viscosity that result from changes in the composition of the sample gas stream), result in changes in the mass rate of flow of the sample stream. As a result, since the calibration of the instrument's output display presupposes a constant bulk mass flow rate, there occurs a discrepancy between the actual concentration value and the displayed concentration value. While such discrepancies are typically on the order of a few percent, they can be of great importance in applications such as auto emission analysis in which small differences in pollutant concentration can make the difference between meeting or not meeting state and federal emission standards.

SUMMARY OF THE INVENTION

In accordance with the present invention, the above described problem is solved by connecting, between the regulated source of sample gas and the sample capillary, a correction signal generating device for developing an output signal that varies in accordance with the bulk mass rate of flow of the sample gas therethrough. The output of this correction device is then combined with the output signal from the instrument's detector assembly, in a signal correcting network, to generate a corrected output signal for application to the output display of the instrument. As a result of the use of the corrected output signal, the output display of the instrument correctly indicates the parts per million concentration of the component of interest, in spite of changes in the mass rate of flow of the sample gas from the value established during the calibration of the instrument.

In the preferred embodiment of the present invention, the correction signal generating device includes a flow sensing device of the type that produces a differential output pressure that is dependent upon the mass rate of flow of gas therethrough, and a pressure transducer of the type that produces an output signal having a magnitude that is substantially proportional to the pressure differential applied thereto. In general, however, any mass flow responsive signal generator may be used to provide the desired correction signal.

In accordance with another feature of the present invention, the flow resistance of the flow sensing device is chosen to be small in relation to the flow resistance of the sample capillary. This assures that the sample capillary is for all practical purposes the only fluidic element for which a flow rate correction must be made and, consequently, that the correction signal corrects for substantially all of the flow rate errors that are associated with the sample capillary.

In accordance with still another feature of the present invention, the flow rate correction signal is algebraically combined with the output signal from the instrument's detector assembly to provide a corrected output signal that correctly reflects the concentration of the component of interest in spite of changes in the bulk mass rate of flow of the sample stream.

DESCRIPTION OF THE DRAWINGS

FIG. 1 is a generalized block diagram of a gas analyzer of a type known in the art, FIG. 2 is a generalized block diagram of a gas analyzer that has been modified in accordance with the present invention.

DESCRIPTION OF THE PREFERRED EMBODIMENTS

Figure 3:
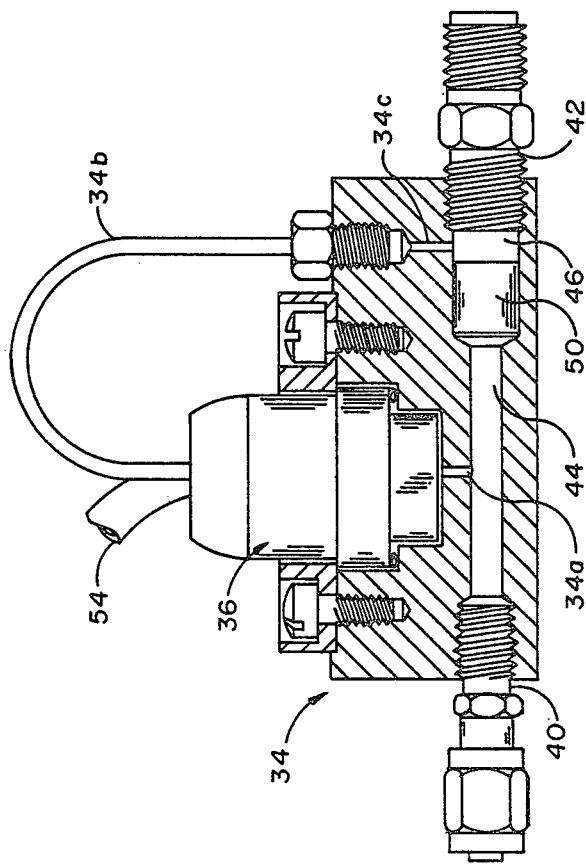
FIG. 3 is a partial cross-sectional view of one illustrative embodiment of a correction signal generating device of a type suitable for use in practicing the present invention.

Referring to FIG. 1, there is shown a block diagram of a gas analyzer of a known type. This analyzer includes an inlet 12 for admitting a stream of sample gas into a detector assembly 14 and an outlet 16 for venting the sample stream to the atmosphere after the detection process is completed. Detector assembly 14 is commonly of the type that includes a detection chamber within which the component of interest of the sample stream is selectively activated, i.e., rendered detectable, by the action of one or more chemical substances that are introduced through one or more inlets such as inlet 18. Detector assembly 14 may in general, however, comprise any type of detection apparatus the output of which is sensitive to changes in the bulk mass rate of flow of the sample stream.

Within or immediately adjacent to the detection chamber is a detector element or transducer which is responsive to the component of interest in its activated state and which, in conjunction with a detector electronic network 20, produces an output signal that is indicative of the intensity of the reaction within detector assembly 14 as a function of time. The latter signal is, in turn, applied to a suitable output indicator 22, such as a galvanometer that is calibrated in terms of the concentration of the component of interest. This concentration is usually expressed in units of parts per million measured on a numerical basis, i.e., the ratio of the number of molecules of interest to the total number of molecules in the sample stream.

During operation, detector network 20 produces a signal which may be visualized as having a succession of instantaneous values each of which reflects the instantaneous quantity of the component of interest within detector assembly 14. Stated differently, the output of detector network 20 is proportional to the mass rate of flow of the component of interest through the detection chamber. If, for example, twice as much of the component of interest passes through detector assembly 14 in one second as passed therethrough in one second when the instrument was calibrated, it may be inferred that the concentration of the component of interest in the sample stream is twice as great as that which existed during calibration. This inference is valid, however, only if the mass rate of flow of the sample stream as a whole (the bulk or overall mass rate of flow) has the same value that existed during calibration. This is because the absolute quantity of the component of interest that flows through detector assembly 14 in a given time can change either as a result of changes in the bulk mass flow rate of the sample stream through detector assembly 14 or as a result of changes in the concentration of the component of interest within the sample stream. The peak or maximum concentration reading will, for example, be twice the value indicated during calibration either (a) if a gas stream having the same concentration of the component of interest that was present during calibration is passed through the instrument at twice the bulk flow rate used during calibration, or (b) if a gas stream having twice the concentration of the component of interest that was present during calibration is passed through the instrument at the same bulk flow rate used during calibration.

In order to deal with the above situation, instrument designers have introduced devices that are intended to maintain the bulk mass rate of flow of the sample stream through detection chamber 14 at a constant value. The devices most commonly used for this purpose include a back pressure regulator 24 connected between sample inlet 12 and the atmosphere and a flow restrictor element 26 such as a sample capillary connected between sample inlet 12 and detector assembly 14. Because detector assembly 14 is vented to the atmosphere and because the pressure drop thereacross is negligible, back pressure regulator 24 effectively fixes the pressure drop across flow restrictor 26. As a result, the bulk mass rate of flow of the sample stream through the fixed flow resistance of capillary 26 and detector chamber 14 is approximately constant. The value of this rate of flow may be adjusted by means of a manual adjustment knob 24a located on back pressure regulator 24, pressure gauge 30 being used to monitor the adjustment process.

During the development of the present invention it was discovered that measurements made on instruments of the above described type can include significant errors. One cause of these errors was found to be the fact that changes in the bulk kinematic viscosity of a gas stream flowing through a flow restriction such as a sample capillary produce corresponding changes in the bulk mass rate of flow of the gas stream, even in the presence of a constant pressure drop across the flow restriction. These changes result from the fact that, for laminar flow, the pressure drop produced by the flow of a gas through a flow restriction proportional not to the bulk mass rate of flow, but rather proportional to the product of the bulk mass rate of flow and the bulk viscosity of the gas.

In auto emission analyzers, for example, it was found that the bulk viscosity of the exhaust gas can change appreciably as engine speed and power are changed during the course of a measurement. This viscosity change, in turn, results from changes in the composition of the exhaust gas, bulk or overall viscosity being dependent upon the individual viscosities of the various components and their respective concentrations. More particularly, the bulk viscosity of a sample stream is equal to the weighted average of the individual viscosities of all of the components of the sample stream, concentration beng the weighting factor. Other factors such as changes in the temperature of the gas may also affect viscosity and thereby the mass rate of flow.

Another cause of these errors was found to be the fact that the diameter and surface slipperiness of the passage through the sample capillary can vary as a result of the formation and dissipation of adsorbed particles, gobs or films of one or more of the chemical substances such as water that are present in the sample stream. The adsorption of a film of water on the interior of a capillary having a smooth interior passage following the calibration of the instrument with a dry gas can, for example, reduce the effective diameter of the passage through the capillary and thereby reduce the mass rate of flow. On the other hand, the adsorption of a film of water on the interior of a capillary having a relatively rough interior passage may obscure the surface roughness thereof and actually increase the mass rate of flow by decreasing the turbulence of that flow. Either of these changes in mass flow rate will, in turn, change the relationship between the detected and displayed quantities of the component of interest from the relationship that was established therebetween during calibration. This source of error may, of course, be operative either instead of or in addition to the above described viscosity-related source of error. Thus, prior to the present invention, the accuracy of instruments of the type that are mass flow rate sensitive has been adversely affected by the failure to correct for changes in mass flow rate produced by a variety of causes.

Referring to FIG. 2, there is shown a gas analyzer that has been modified in accordance with the present invention to correct for changes in the bulk mass rate of flow of the sample gas stream, corresponding parts in FIGS. 1 and 2 being similarly numbered. The instrument shown in FIG. 2 differs from that shown in FIG. 1 in that the instrument of FIG. 2 includes correction signal generating means 32, which may include a flow sensing device 34 and a pressure transducing device 36, and signal correcting means 38, which may take the form of the electronic circuitry shown in FIG. 4. One illustrative embodiment of correction signal generator 32, in which flow swnsor 34 and pressure transducer 36 are included in a single assembly, is shown in FIG. 3.

Correction signal generator 32 is connected in series with sample capillary 26 and serves to generate on output conductor 32a therefore an electrical correction signal that varies in accordance with the bulk mass rate of flow of the sample stream therethrough. This signal is applied to signal correcting network 38 along with the output signal from detector electronic network 20. Within correcting network 38, these signals are algebraically combined to produce a corrected output signal for application to output indicator 22. In accordance with an important feature of the present invention, the corrected output signal has a magnitude which accurately reflects the concentration of the component of interest, even when the bulk mass rate of flow of the sample gas stream deviates from the mass rate of flow established during the calibration of the instrument.

Assume, for example, that the bulk viscosity of the sample gas increases by one percent, while the concentration of the component of interest remains constant. (This condition might occur if the concentration of a relatively more viscous component-not-of-interest increases while the concentration of another relatively less viscous component-not-of-interest decreases and the concentration of the component of interest remains constant.) Under these conditions the bulk mass rate of flow through capillary 26 and detector assembly 14 will decrease by one percent, causing a one percent reduction in the output signal which detector network 20 applies to correcting network 38 through conductor 20a. At the same time, the decreased mass flow rate through flow sensor 34 will cause a one percent decrease in the correction signal that is applied to network 38 through conductor 32a. In accordance with the present invention, correcting network 38 combines the latter signals in such a way that output indicator 22 is supplied with a corrected output signal that is unchanged from its original value.

Figure 4:
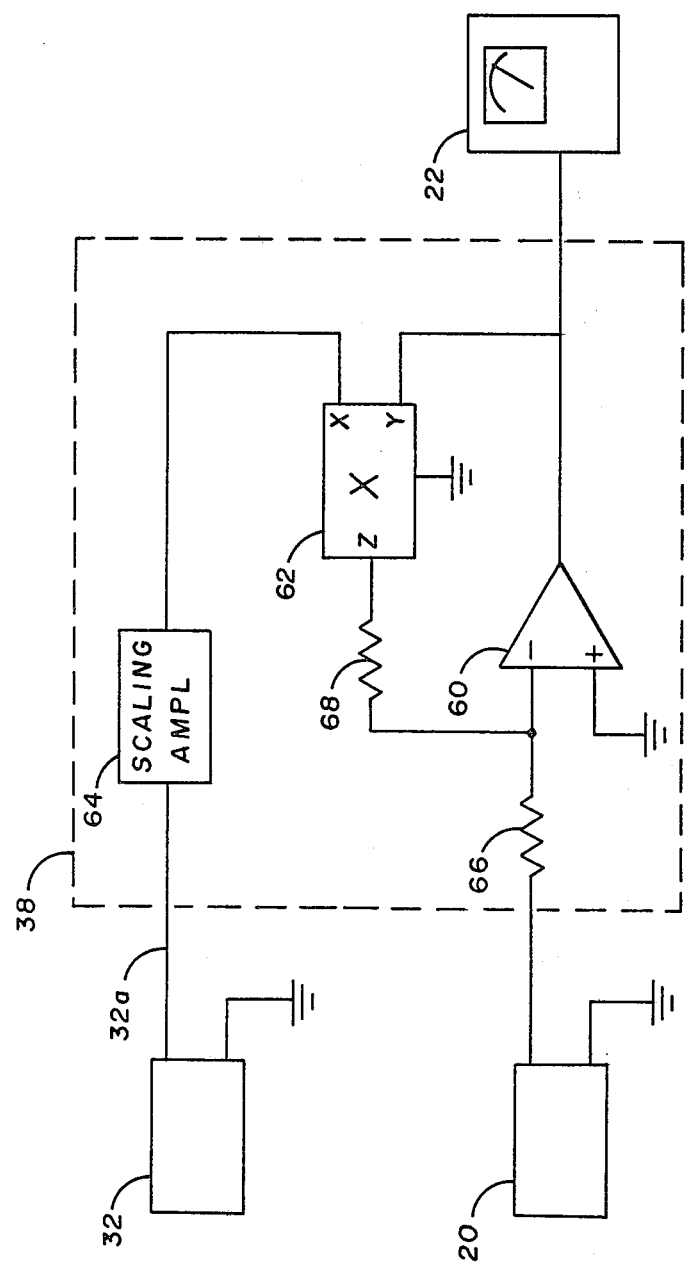
FIG. 4 is a schematic-block diagram of one illustrative correcting network of a type suitable for use in practicing the present invention.

In the embodiment of correcting network 38 that is shown in FIG. 4, the corrected output signal is generated by dividing the output signal from detector network 20 by a signal proportional to the signal produced by correction generator 32, in a suitable analog divider circuit, and by applying the result of the division to output indicator 22. In this manner the above mentioned decrease in the magnitude of the output signal from detector network 20 is counteracted by the magnitude increasing effect of dividing that signal by a correction signal of reduced magnitude.

Conversely, if the bulk viscosity of the sample gas should decrease by one percent while the concentration of the component of interest remains constant, the mass rate of flow through capillary 26 and detector assembly 14 will increase by one percent, causing a one percent increase in the signal which detector network 20 applies to correcting network 38. At the same time, however, the increased mass flow rate through flow sensor 34 will cause an increase in the magnitude of the correction signal on conductor 32a. Under these conditions, correcting network 38 uses the one percent increase in the output signal of detector network 20 to counteract the one percent increase in the correction signal and thereby assures that output indicator 22 is supplied with a corrected signal that is unchanged from its original value.

Similarly, if the concentration of the component of interest should change while the bulk viscosity of the sample gas remains constant, there will be no change, in the mass rate of flow of the sample stream and, therefore, no change in the magnitude of the correction signal. Such a condition might occur, for example, if the change in bulk viscosity that results from a change in the concentration of the component of interest is offset by changes in bulk viscosity that result from changes in the concentration of the remaining components. Under these conditions, the corrected output signal from correcting network 38 will change only as necessary to follow changes in the concentration of the component of interest, and the correction signal from generator 32 will have no adverse effect.

It will be understood that if the concentration of the component of interest and the bulk viscosity of the sample gas should change at the same time, the effect produced by correction signal generator 32 and correcting network 38 will be somewhere between the effects produced in the above-described examples. More particularly, elements 32 and 38 will offset the error producing effect of changes in the viscosity of the sample gas, but will not inhibit the effect of real changes in the concentration of the component of interest.

A similar sequence of corrective activities will be understood to occur in the presence of changes in mass flow rate that occur as a result of purely physical causes, such as the adsorption of films on the interior surfaces of the sample capillary. Such corrective activities are accomplished in the manner described above and at the same time as any corrections necessitated by bulk viscosity changes. This is possible because the degree of correction provided by the present invention is dependent only on the bulk mass rate of flow of the sample stream and may therefore be directly measured by correction signal generator 32 after all influences thereon have exerted their various (sometimes offsetting) effects. Thus, the apparatus of the invention will afford measurements of improved accuracy in the presence of all types and combinations of types of sample gas flow conditions.

In order that correction signal generator 32 may provide a correction signal that accurately reflects changes in the mass rate of flow of the sample stream, it is desirable that certain relationships exist between the variables that govern the operation of the apparatus of the invention. Firstly, the flow resistance of flow sensor 34 should be small in comparison with the flow resistance of sample capillary 26. This relationship assures that the pressure difference between the inlet and outlet of flow sensor 34 is negligible in comparison with the pressure drop across sample capillary 26. The latter relationship, in turn, assures that the mass rate of flow through flow sensor 34 is substantially independent of the flow resistance thereof and that flow sensor 34 does not appreciably affect the bulk mass rate of flow of the sample stream.

A second desirable relationship is that the flow of the sample stream should be substantially laminar, i.e., have a Reynolds number less than approximately 2,000. This relationship assures that the pressure drop across sensor 34 and capillary 26 are substantially proportional to the mass rate of flow of the sample gas. This proportionality is, in turn, desirable because it allows the use of a correcting network 38 having only first order terms in its transfer function. It will be understood, however, that the pressure drop across flow sensor 34 need not be linearly related to the flow rate therethrough, provided that correcting network 38 is constructed so that it can receive the resulting nonlinear correction signal and provide the desired correction to the output signal of detector network 20.

A third desirable relationship is that the rate of change of the pressure drop across the flow sensor with respect to changes in the mass rate of flow therethrough $(dP/dM)$ be relatively greater than the rate of change of the pressure drop across the flow sensor with respect to changes in viscosity of the gas flow therethrough $(dP/d\mu)$. This may be easily accomplished by simply choosing relatively low mass rates of flow for the sample stream. The meeting of this relationship assures that the magnitude of the correction signal is dependent upon the mass rate of flow of the sample gas and virtually independent of the viscosity thereof. The latter result, in turn, assures that changes in mass rate of flow of the sample stream can be accurately sensed, in spite of the fact that the fluid flow equation governing the operation of flow sensor 34 may have the same general mathematical form as that govering the operation of sample capillary 26.

A first combined effect of the above relationships is that, for sample capillary 26, the pressure set by back pressure regulator 24 is the forcing function and the mass rate of flow therethrough is inversely proportional to the viscosity of the sample gas. A second combined effect is that, for sensor 34, mass rate of flow is the forcing function and viscosity is not an important factor in determining the pressure drop thereacross. Together, these effects assure a correction signal having a magnitude that accurately reflects the needed degree of output correction.

A number of flow sensors that are of the type which may be used to implement flow sensor 34 are known in the art. Two such sensors are described in U.S. Pat. No. 3,349,619 granted in the name of G. H. Millar on Oct. 31, 1967 and U.S. Pat. No. 4,118,973 granted in the name of Tucker et al. on Oct. 10, 1978. A number of pressure transducers of the type which may be used to implement pressure transducer 36 are also known in the art. The preferred embodiment of correction signal generator 32, however, combines flow sensor 34 and pressure transducer 36 in a single convenient assembly. A partial cross-sectional view of one illustrative assembly of this type is shown in FIG. 3.

Referring to FIG. 3, it will be seen that the illustrated assembly includes a flow sensing device 34 having an inlet tube 40 and an outlet tube 42, which tubes are connected together by an internal flow path that includes duct sections 44 and 46 having differing diameters. Also included in this flow path is a sintered metal plug 50 having a size and porosity suitable for assuring that the flow through flow path 44-46 is substantially laminar.

The assembly of FIG. 3 also includes a differential pressure transducer 36 having an input/output cable 54 through which suitable d.c. biasing voltages may be supplied to transducer 36 and through which the desired correction signal may be supplied to correcting network 38. The pressure transducer illustrated in FIG. 3 is preferably of the type which includes a pressure sensitive diaphragm, one side of which is exposed to duct section 44 through a hole 34a and the other side of which is exposed to duct section 46 through a connecting tube 34b and a hole 34c. Mounted on this diaphragm is a strain gauge sensing element that is connected as a part of a Wheatstone bridge network. With this configuration the electrical output of the bridge network varies with the resistance of the strain gauge, which, in turn, varies with the deflection which the pressure difference between duct sections 44 and 46 produces on the diaphragm. Because devices of the general type illustrated in FIG. 3 are known to those skilled in the art, the operation thereof will not be described in detail herein.

To the end that the output signal from control signal generator 32 may be combined with the output signal from detector network 20 to provide a corrected output signal to output indicator 22, there is provided the correcting network shown in FIG. 4. Correcting network 38 includes an analog divider network comprising an operational amplifier 60 and an analog multiplier device 62 which may be an integrated circuit of the type sold under the commercial designation AD534 or, in general, any other type of circuit or network having an analog multiplying characteristic. Correcting network 38 also includes a scaling amplifier 64 for adjustably increasing the magnitude of the correction signal to a level suitable for application to multiplier 62, and suitable current limiting resistors 66 and 68 for fixing the ratio of the currents that are applied to amplifier 60 by detector network 20 and multiplier 62.

In operation, multiplier 62 serves to apply to one input of amplifier 60 a negative feedback signal that is proportional to the product of the correction signal from correction generator 32 and the output voltage of amplifier 60. In response to the currents established by these voltages, amplifier 60 applies to output indicator 22 a corrected output signal that is proportional to the output voltage of detector network 20 divided by the correction signal from correction generator 32. The reason why this corrected output signal is free of errors resulting from changes in the mass rate of flow of the sample stream was explained in connection with FIG. 2 and will not, therefore, be discussed further herein. In addition, because the manner in which analog division is accomplished by an amplifier-multiplier circuit is well-known to those skilled in the art, the internal operation of correcting network 38 will also not be further described herein.

While the embodiment of correcting network 38 that is illustrated in FIG. 4 includes an analog divider, it will be understood that correcting network 38 may, in general, include any electronic circuit which will algebraically combine the signal from correction generator 32 with the output signal from detector network 20 to produce the desired corrected output signal. If, for example, the apparatus shown in FIG. 2 is a part of a larger instrument or system that includes a digital computer, the desired signal combining activity may be provided by introducing known algebraic subroutines into the overall program or by invoking subroutines of this type that are already present. Such approaches are, however, subject to the disadvantages that suitable analog to digital converters must be provided and that relatively high signal sampling rates must be used if an apparently continuous output reading is to be provided.

The application of the invention to certain specific instruments will now be described in connection with FIGS. 5 and 6, corresponding parts in all Figures being similarly numbered.

Figure 5:
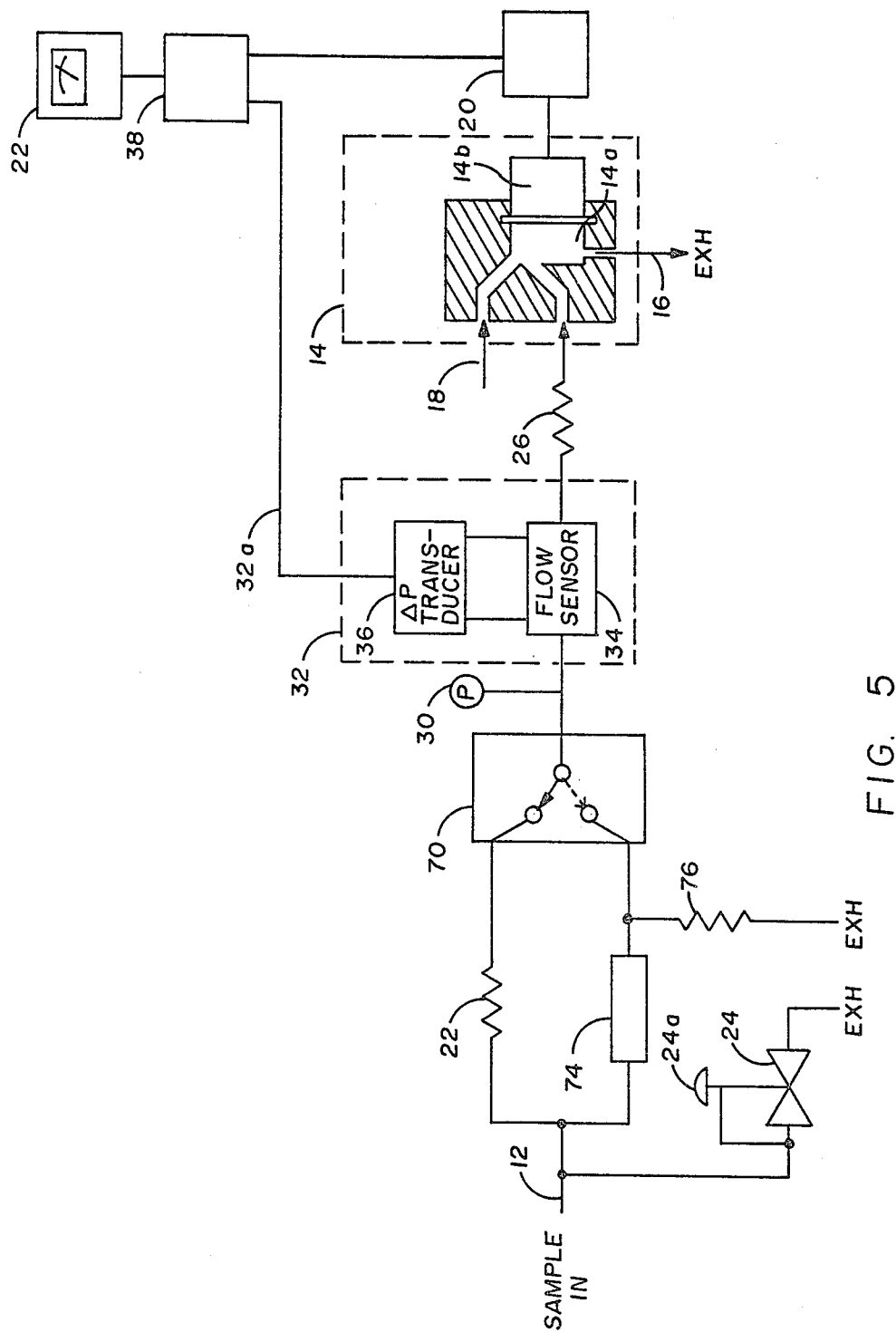
FIG. 5 is a block diagram of a chemiluminescent gas analyzer that has been constructed in accordance with the invention.

Referring to FIG. 5 there is shown, partly in block form and partly in cross-sectional form, a gas analyzer of the chemiluminescent type, that is, an analyzer in which the concentration of a component of interest in a sample stream is measured by means of the light emitted when that component reacts chemically with a reactant that is introduced into the instrument as a part of a reactant gas stream. If, for example, the quantity to be measured is the nitric oxide (NO) content of the exhaust of an automobile engine, a sample of the exhaust is introduced into detection chamber 14a through sample capillary 26 and a reactant substance (typically a mixture of air and ozone) is introduced into detection chamber 14a through inlet 18.

The component of interest and the reactant substance are preferably introduced at one end of the detection chamber in a manner which assures the thorough mixing thereof, the size and arrangement of the detection chamber being such that substantially all of the luminous energy produced by the resulting chemical reaction can be detected by a detector transducer such as photomultiplier 14b before being exhausted to the atmosphere through outlet 16. The resulting signal, after amplification by detector electronic network 20, is applied to correcting network 38 wherein it is combined with the signal from correction signal generator network 32 to provide the desired corrected output signal. This corrective activity occurs in the manner described in connection with FIG. 2 to provide an output indication that is corrected for changes in the mass rate of flow through sample capillary 26.

Because oxides of nitrogen ordinarily occur as a mixture of oxides ($NO_x$) with differing amounts of oxygen, e.g., NO and $NO_2$, it has often been found necessary to measure the total $NO_x$ concentration in two or more stages. This multi-stage measurement may be made, in the presence of the present invention, by using the stage selecting elements shown at the left side of FIG. 5.

These elements include a two-position select valve 70 having a first (solid line) position in which the sample is applied to detection chamber 14a through a sample capillary 72, the function of which will be described presently, and a second (dotted line) position in which the sample stream is applied to detection chamber 14 through a reactor tube 74 which may be filled with hot glassy carbon. Neither of the two positions of select valve 70 interfere with the practice of the invention, however, because the pressure gauge 30 which is used during the calibration of the instrument is located downstream of select valve 70.

When select valve 70 is in its first position, detector 14a detects the nitric oxide concentration of the sample gas as the nitric oxide is oxidized to nitrogen dioxide by the ozone that is introduced into detection chamber 14a through inlet 18. For this condition, the nitrogen dioxide originally present in the sample does not affect the output reading because it is already fuly oxidized. When, however, select valve 70 is in its second position, the sample stream enters detector assembly 14 through reactor 74. As a result, the nitrogen dioxide that is present in the sample is reduced by the hot carbon to a mixture of nitric oxide and carbon monoxide which, along with the nitric oxide already present in the sample, is measured in detector assembly 14. The reading obtained when select valve 70 is in its first position is then taken as the NO concentration and the nitrogen dioxide content of the original sample is calculated from the increased reading obtained when select valve 70 is switched from its first to its second position. When used in this manner, capillary 72 substantially balances the flow resistance of reactor 74 when select valve 70 is in its second position, and capillary 76 is used as a bleeder to sustain a condition-maintaining flow through reactor 74 when select valve 70 is in its first position.

Because the composition of the sample stream is different for the two positions of select valve 70, the bulk viscosity of the sample stream can also be expected to be different. As a result, different bulk mass rates of flow of the sample stream may occur as the position of select valve 70 is moved between its two positions. It will be understood that the present invention will compensate for any such internally caused differences in mass flow rate as well as for any differences in mass flow rate that are cuased by events occurring outside of the instrument.

Figure 6:
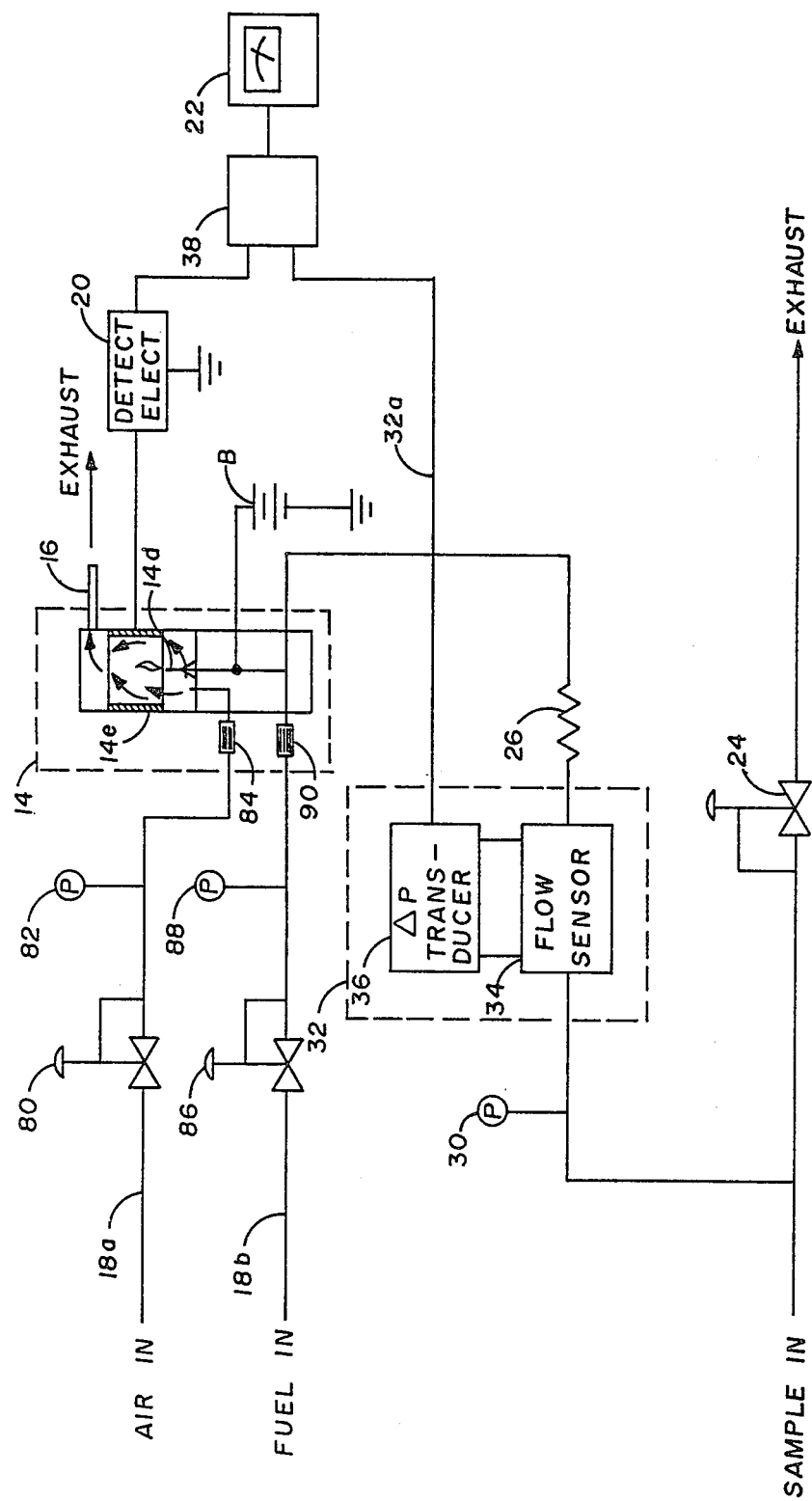
FIG. 6 is a block diagram of a gas analyzer of the flame ionization type that has been constructed in accordance with the present invention.

Referring to FIG. 6 there is shown, partly in block and partly in cross-sectional form, a drawing of the present invention as applied to a gas analyzer of the flame ionization type. In a typical application of an instrument of this type, the hydrocarbon concentration of a sample is determined from the magnitude of the current flow which a biasing source B produces between a burner-electrode 14d and a ring shaped collector electrode 14e as the sample is burned within detector assembly 14. In instruments of this type, predetermined standard combustion conditions are established by mixing the sample gas from capillary 26 with a regulated flow of fuel and by burning the mixture in a regulated flow of air, the fuel and air being introduced through inlets 18b and 18a, respectively. Once the desired fuel and air flow conditions are established by adjusting pressure regulators 80 and 86 in conjunction with pressure gauges 82 and 88, respectively, and once the desired sample flow rate is established by adjusting pressure regulator 24 in conjunction with pressure gauge 30, detector electronic network 20 provides to output indicator 22 an output signal that is intended to be proportional to the hydrocarbon content of the sample gas.

As in the case of the chemiluminescent analyzer described in connection with FIG. 5, however, the flame ionization analyzer is sensitive to changes in the mass rate of flow of the sample stream, which rate is in turn dependent on the viscosity of the sample gas, in spite of the constant pressure established by pressure regulator 24. Also as in the case of the analyzer of FIG. 5, errors resulting from spurious changes in mass flow rate are eliminated by connecting a correction signal generator of the previously described type in series with sample capillary 26, and by connecting a correcting network 38 of the previously described type between detector network 20 and output indicator 22. Because the operation of these devices is the same as that described previously in connection with FIG. 2, the operation thereof will not be further described herein.

While the apparatus of the invention has been described with reference to certain specific embodiments, the true scope thereof should be determined with reference to the following claims.

What is claimed is:

1. In a gas analyzer having a detector assembly for receviing a sample gas stream and for producing an output signal that varies in accordance with the mass rate of flow of a component of the sample gas stream, a flow restricting element for limiting the rate at which the sample gas stream is admitted into the detector assembly, and an output indicator for displaying the concentration of said component, the improvement comprising:
   (a) correction signal generating means for generating a correction signal that varies in accordance with the mass rate of flow of the sample gas stream, and
   (b) correcting means for applying to said output indicator a corrected output signal that varies in accordance with the output signal of said detector assembly and said correction signal.

2. A gas analyzer as set forth in claim 1 in which said analyzer is of the chemiluminescent type.

3. A gas analyzer as set forth in claim 1 in which said analyzer is of the flame ionization type.

4. A gas analyzer as set forth in claim 1 in which said correcting means includes means for algebraically combining said output signal and said correction signal.

5. A gas analyzer as set forth in claim 4 in which said correcting means includes analog dividing means.

6. A gas analyzer as set forth in claim 1 in which said correction signal generating means includes a flow sensing device connected in series with said flow restricting element.

7. A gas analyzer as set forth in claim 6 in which the flow resistance of said flow sensing device is small in relation to the flow resistance of said flow restricting element.

8. A gas analyzer as set forth in claim 6 in which the flow of gas through said flow sensing device is substantially laminar.

9. A gas analyzer as set forth in claim 6 wherein said flow sensing device is a device in which the rate of change of the pressure drop thereacross with respect to changes in the mass rate of flow of gas flowing therethrough is large in relation to the rate of change of the pressure drop thereacross with respect to changes in the viscosity of gas flowing therethrough.

10. A gas analyzer as set forth in claim 6 in which said correction signal generating means includes a pressure transducer for generating a correction signal that is dependent upon the pressure drop across said flow sensing device and means for connecting said pressure transducer to said flow sensing device.

11. In a gas analyzer having a detector assembly for receiving a sample gas stream and for producing an output signal that varies in accordance with the mass rate of flow of a component of the sample gas stream, a pressure regulator, a sample capillary connected between the pressure regulator and the detector assembly, and an output indicator for displaying the concentration of said component, the improvement comprising:
   (a) a flow sensing device, connected in series with said capillary, for developing a pressure that is dependent upon the mass rate of flow of said sample gas stream through said capillary,
   (b) a pressure transducer for generating a correction signal that is dependent upon the pressure developed by said flow sensing device, and
   (c) a correcting network for receiving the output signal of said detector assembly and said correction signal, and for combining those signals to provide to said output indicator a corrected output signal that is free of errors caused by changes in the mass rate of flow of the sample stream through said capillary.

12. A gas analyzer as set forth in claim 11 in which the flow resistance of said flow sensing device is small in relation to the flow resistance of said sample capillary.

13. A gas analyzer as set forth in claim 12 in which the flow of gas through said flow sensing device is substantially laminar.

14. A gas analyzer as set forth in claim 13 wherein said flow sensing device is a device in which the rate of change of the pressure drop across said flow sensing device with respect to changes in the mass rate of flow of gas flowing therethrough is large in relation to the rate of change of the pressure drop across said flow sensing device with respect to changes in the viscosity of gas flowing therethrough.

15. A gas analyzer as set forth in claim 14 in which said correcting network combines said correction signal and the output signal of said detector assembly by forming the algebraic product of a first term dependent upon said output signal and a second term dependent upon said correction signal.

16. A gas analyzer as set forth in claim 15 in which said correcting network includes an analog divider.

* * * * *